United States Patent
Wilson et al.

[11] Patent Number: 5,344,318
[45] Date of Patent: Sep. 6, 1994

[54] AESTHETIC INTRAMOBILE ELEMENT FOR DENTAL IMPLANTS

[76] Inventors: Richard S. Wilson; Barry F. Sukoneck, both of 2401 Pennsylvania Ave., Suite 1A8, Philadelphia, Pa. 19130; Kenneth C. Wenzer, 11538 February Cir., Apt. 402, Silver Spring, Md. 20904

[21] Appl. No.: 159,319

[22] Filed: Nov. 30, 1993

[51] Int. Cl.⁵ .................... A61C 13/28; A61C 13/12; A61C 13/225; A61C 8/00
[52] U.S. Cl. .................... 433/169; 433/177; 433/173
[58] Field of Search ............... 433/169, 172, 173, 174, 433/175, 176, 177

[56] References Cited

U.S. PATENT DOCUMENTS

| | | | |
|---|---|---|---|
| 4,756,689 | 7/1988 | Lundgren et al. | 433/169 X |
| 5,049,072 | 9/1991 | Lueschen | 433/177 X |
| 5,098,294 | 3/1992 | Lee et al. | 433/169 |
| 5,125,839 | 6/1992 | Ingber et al. | 433/169 |

*Primary Examiner*—Gene Mancene
*Assistant Examiner*—Nicholas D. Lucchesi
*Attorney, Agent, or Firm*—Robert Halper

[57] ABSTRACT

An intramobile element for dental implants that includes an elastic, flat, circular washer having rounded edges, being 0.75 mm in height and designed to fit neatly on existing abutments and a prosthesis that comprises a gold member to which a porcelain cover is cast. The gold member has a cylindrical head with an internal cradle to precisely support a gold retaining screw with a rounded head and a screw channel spaced from the screw threads to allow for rotation of the prosthesis and making use of existing specific length abutments to control placement of the washer either supragingivally for hygienic reasons or supragingivally for esthetic reasons.

6 Claims, 3 Drawing Sheets

AESTHETIC INTRAMOBILE ELEMENT FOR DENTAL IMPLANTS

FIELD OF THE INVENTION

The invention relates to a dental implant single intramobile element (IME) and to a special prosthesis designed to dampen the transmission of occlusal forces into the jawbone. More specifically, the invention is an implant system which:

1) Allows aesthetic fabrication of implant restorations.
2) Is hygienic.
3) Is elastic and yet allows precise, predictable seating of a restoration in three-dimensional space, in other words, it establishes a precise vertical dimension of occlusion.
4) Utilizes existing fixture and abutment components, eliminating the need for retooling by manufacturers.

BACKGROUND OF THE INVENTION

Root-form dental implants have been used with success rates of over 90% to replace teeth lost to various disease processes. The initial clinical use was to replace 12 to 14 teeth per arch on 6 to 8 implants. This is in the fully edentulous situation, and is rigidly fixed in place by retaining screws. In recent years many more applications have evolved in the partially edentulous patient. These include fixed bridges on as few as two implants, but lacking the tripod effect provided by three or more implants. These also include single tooth restorations, that is one tooth on one implant. The long-term success rates of these more recent types of restorations are not known.

Current implant restorations typically conduct occlusal forces through porcelain, gold alloy, titanium, then to bone. All of these structures are rigidly fixed together with screws.

Implants generally consist of three components. The *fixture*, fabricated in titanium, is surgically placed into the jawbone. A process called osseointegration occurs, in which bone forms a direct contact with the titanium fixture. Any fibrous tissue or other tissue type is considered to be a lack of osseointegration and constitutes a clinical failure of the implant fixture. In fully edentulous cases, failure of one or two of, say, eight implant fixtures does not cause the entire prosthesis to fail. However, in partially edentulous and single tooth applications, failure of even one implant fixture normally results in failure of the entire case. A new fixture can subsequently be placed, but this considerably delays the case and there is no guarantee that the new fixture will work either. It should be noted that approximately 50% of failures occur before loading with occlusal forces via a prosthesis, and most of the remaining failures occur within one year of each loading.

The second implant component is the abutment, which is a cylindrical titanium construct with a large titanium abutment retaining screw. The abutment is precisely machined to fit the fixture; any abutment should fit any fixture with the same degree of exactness. The abutment passes from the distal surface of the fixture through the gingival tissue. Various abutment types are available. Some pass entirely through the gingiva so that their distal surface is visible in the mouth. Others end subgingivally for better aesthetics. Aesthetics depends on the contour of the restoration and the exact position of the distal surface of the abutment.

The third implant component is the *prosthesis*. This is custom-cast gold alloy with a veneer of porcelain, and forms the actual "teeth". Casting is accomplished by either:

1) A plastic cylinder, fitting to the distal surface of the abutment, which is cast in the lost wax technique, or
2) A machined gold alloy to which additional gold can be cast to form the tooth.

Porcelain is added after the metal frame is cast. The prosthesis is rigidly held in place by one or more prosthesis retaining screws. These are smaller than the abutment retaining screws and are made from gold, not titanium. Both screws are tightened with 5 to 10 Newtons of torque; this process causes the fixture-abutment-prosthesis assembly to be held rigidly together.

Restorations on implants can be esthetic enough that they resemble natural teeth in color, contour and relationship to the gingiva. Titanium and gold can be hidden in the subgingival area, the *sulcus*. In these restorations, contoured and shaded porcelain can be carried below the gingival crest, into the subgingival area. For technical reasons, this porcelain must end 1 mm above the proximal surface of the abutment. Consider the example of a 4 mm sulcus (the distance from the crest of the gingiva to the distal surface of the fixture). If the desired result is a porcelain, natural tooth growing out of the gingiva, the abutment can be no more than 2 mm in height. This leaves 1 mm for the minimum metal showing on the prosthesis and 1 mm of subgingival porcelain as a reserve in the case of recession or shrinkage of the gingiva.

Thus, many of the drawbacks of earlier implant restorations, particularly aesthetics deficits, have been overcome. However, concern has arisen over the rigidity of the complete implant system. The system possesses a very high *modulus of elasticity*, which means that it has very little dimensional change per unit of force applied. Occlusal forces are transmitted in a direct manner through the entire system into the bone. Some concerns are:

1) The natural tooth possesses a periodontal ligament, which dampens occlusal forces. Lacking this dampening may cause failure (fracture or bending) of implant components. Indeed, the prosthesis retaining screw is gold and smaller than the titanium abutment retaining screw. This provides a "weak link"; the easiest component to break is also the easiest to remove and replace. Thus, implant design anticipates some percentage of component failure.

2) Fixed bridges from natural teeth to implants have historically had poor success rates. The implants are so rigid that they support the restoration while the teeth drift out of function. The resulting torque may cause restoration failure or implant component fracture.

3) The different pattern of stress induced by the more direct force transmission may cause failure of the bone-titanium interface (osseointegration). Long-term (>10 year) studies on this aspect of the partially edentulous and single tooth situations do not exist.

4) Extreme accuracy of fit is required between the prothesis and the superior surface of the abutment. Any minor imperfections in impression making and prosthesis fabrication become exceedingly damaging due to the lack of elasticity. The strain induced by these inaccuracies may cause failure of the bone-titanium interface.

Various intramobile elements have been designed to simulate the function of the healthy periodontal ligament as occlusal function is transmitted through the restoration. Such function in humans varies on a range of 100–2,440 Newtons in an axial direction, and is on the order of 20 Newtons in a lateral direction. A healthy periodontal ligament may depress and rebound 0.1 mm. An implant prosthesis, being rigid, will depress several orders of magnitude less. The goal of an intramobile element is to provide an implant system with a degree of movement under function which is similar to that of a natural tooth.

DESCRIPTION OF THE PRIOR ART

A number of patents and publications which illustrate the state of the art, including fixtures, abutments, prostheses and accessories such as tightening screws, alloys, metals and dampening gaskets will be discussed below. Patents which are deemed to be most pertinent will be related in terms of the following features, deemed illustrative of the invention.

1) Aesthetics, 2) Location, 3) Rotational movement, 4) Changes in vertical dimension of occlusion, 5) Use of existing vs new fixtures/abutments, 6) Relative ease of replacement.

1) Aesthetics

U.S. Pat. Nos. 4,950,161, 4,993,950, 5,026,280, 5,040,982, 5,098,294 and 5,174,755 all show large areas of their elastic components supragingivally.

U.S. Pat. Nos. 4,488,874, 4,547,156, 4,631,031, 4,756,689, 4,993,950 5,026,280, 5,040,982, 5,098,294 and 5,174,755 cannot maintain a natural, physiologic, aesthetic emergence profile, defined as the contours of the implant prosthesis resembling a natural tooth in its relation to the gingival contours as it passes through the gingiva as previously described. The involves bringing porcelain subgingivally.

2) Location-subgingival vs supragingival

Placement of an elastic member on the distal surface of the various abutments provides control of its final position, supragingival or subgingival to an exact depth. Supragingival is more hygenic; subgingival is more aesthetic. Logical clinical decisions could be made based on esthetic and oral hygiene access perameters in various areas of the mouth.

U.S. Pat. Nos. 4,631,031, 4,993,950, 5,026,280, 5,049,982, 5,098,294 and 5,174,755 are all supragingival by nature.

U.S. Pat. No. 4,950,161 is possibly subgingival, but by a standard, non-adjustable amount.

3) Rotational movement during lateral function

In U.S. Pat. No. 4,631,031 threaded stud 40 and crown connector 18 do not allow rotation. In U.S. Pat. No. 4,756,689 flat surfaces between locking screw 4 and matrix 6 do not allow rotation. In U.S. Pat. No. 4,993,950 slight rotation is allowed by the screw, but it is minimal. Flat surfaces between screw 30 and keeper 32 are too long and parallel. U.S. Pat. Nos. 5,026,280 and 5,174,755 allow too much rotational movement. It is excessive compared to natural teeth. In U.S. Pat. No. 5,098,294 the prosthesis is locked in place by a screw. It relies on loose fit to rotate somewhat.

4) Changes in vertical dimension of occlusion with different degrees of retention screw tightening.

U.S. Pat. Nos. 4,631,031, 4,950,161, 4,993,950 and 5,098,294 would appear to compress to various degrees depending on the degree of retaining screw tightening, due to the relatively thick cross sections of their elastic members. U.S. Pat. No. 5,040,982 would compress to various degrees due to the composite nature of its elastic bushing. U.S. Pat. Nos. 5,026,280 and 5,174,755 would also compress to varying degrees due to the large, irregular shape and imprecise fit of their elastic components. For example, a 5% dimensional change in a 5 mm elastic component is much more severe than a 5% change in a 0.75 mm elastic component, when considered as a linear measurement. Such dimensional changes would affect the height of the restoration in an unpredictable manner, which is unacceptable from a functional standpoint.

5) Use of existing vs. new fixtures/abutments.

U.S. Pat. Nos. 4,547,156, 4,631,031, 4,950,161 and 5,098,295 would require new fixture, abutment and prosthesis components, an entirely new system.

U.S. Pat. Nos. 4,488,974, 4,756,689, 4,993,950, 5,026,280, 5,040,982, 5,098,294, and 5,174,755 would require new abutment and prosthesis components, while retaining existing features. Thus no previous intramobile elements have utilized the newer, more esthetic abutment designs.

6) Relative ease of replacement when worn.

U.S. Pat. Nos. 4,547,156, 4,631,031, 5,040,982, 5,098,284, and 5,098,295 appear cumbersome and time-consuming to change in clinical dentistry. Placing very small parts accurately into position while stabilizing and assembling the rest of the prosthesis would be difficult.

Considering all the limitations of the prior art as shown by the above cited patents, there is clearly a need for an esthetic, precisely positioned intramobile element with potential for rotational as well as axial movement of the proper amount.

SUMMARY OF THE INVENTION

The invention utilizes the existing conventional features and abutments of a number of dental manufactures these products could be used. It is the object of this invention to provide for these existing systems a resilient or elastic member and a prosthesis design which allows axial and rotational movement similar to a healthy periodontal ligament on a natural tooth.

It is a further object of this invention to maintain a high degree of control of aesthetic, meaning the concealment of metals and elastic materials where their visibility would be objectionable to the patient.

It is a further object of the invention to allow precise positioning (especially in height or vertical dimension of occlusion) when the prosthesis retention screw is tightened intra-orally.

The invention consists of an elastic member, hereinafter referred to as the *gasket*, and a specific prosthesis/prosthesis retaining screw assembly. The majority of abutments have a flat surface at the perimeter of their distal surface. The central portion of this distal surface is contoured in various complex fashions to allow for placement of the abutment retaining screw and for the particular fit of the prosthetic component.

The gasket portion is a flat, washer-shaped circular construct whose proximal surface rests on the flat portion at the perimeter of the distal surface of the abutment. The gasket is fixed in space by both its inner circular aspect engaging the abutment center and by being compressed between the prosthesis and the abutment distal surface.

The prosthesis portion has a centrally located non-threaded channel for a retention screw. Because there is a space between the threads of the screw and the walls of the channel, rotation of the entire prosthesis can occur under lateral, occlusal forces.

When a direct axial load is applied to the prosthesis, the gasket will compress. Its modulus of elasticity is such that the compression is approximately 0.1 mm, the same as that of a healthy periodontal ligament during an average occlusal load. When lateral components of force occur, the round shape of the prosthesis/prosthesis retention screw interface will allow rotation and a differential compression of the gasket, more on the side of greater occlusal loading. This combination of the round shape and the shaped gasket will dampen the force transmitted into the titanium fixture and the bone.

An inherent problem with elastic members of implant systems is that they have the potential to alter the vertical dimension of occlusion in an unpredictable manner. In other words, if a clinician overtightens a retaining screw, the prosthesis will depress and be in hypofunction. In the present invention the gasket is intended to have a high enough modulus of elasticity so that the 10 Newtons of average torque that a clinician applies to the prosthesis retention screw will not cause significant gasket compression. However, the direct axial loads applied by patient's occlusal forces, being 10 to 200 times greater, will cause the desired gasket compression. The desired precise positioning of implant components is still achieved, since the gasket adds a 0.75 mm component to the system. This component cannot be altered by variations in tightness of prosthesis retention screws, as occurs with different clinicians.

Aesthetic is controlled by placment of the gasket at various levels, using the distal surface of the abutment as a reference point. If this surface is 2 mm below the top of the subgingival surface, the gasket will be invisible. On the other hand if aesthetic is not a concern, the gasket can be in the supragingival, most hygienic position. In any event, the clinician has complete control on a tooth-by-tooth basis, something not previously achievable with previous intramobile elements.

DETAILED DESCRIPTION OF THE PREFERRED EMBODIMENTS

Figure 1:
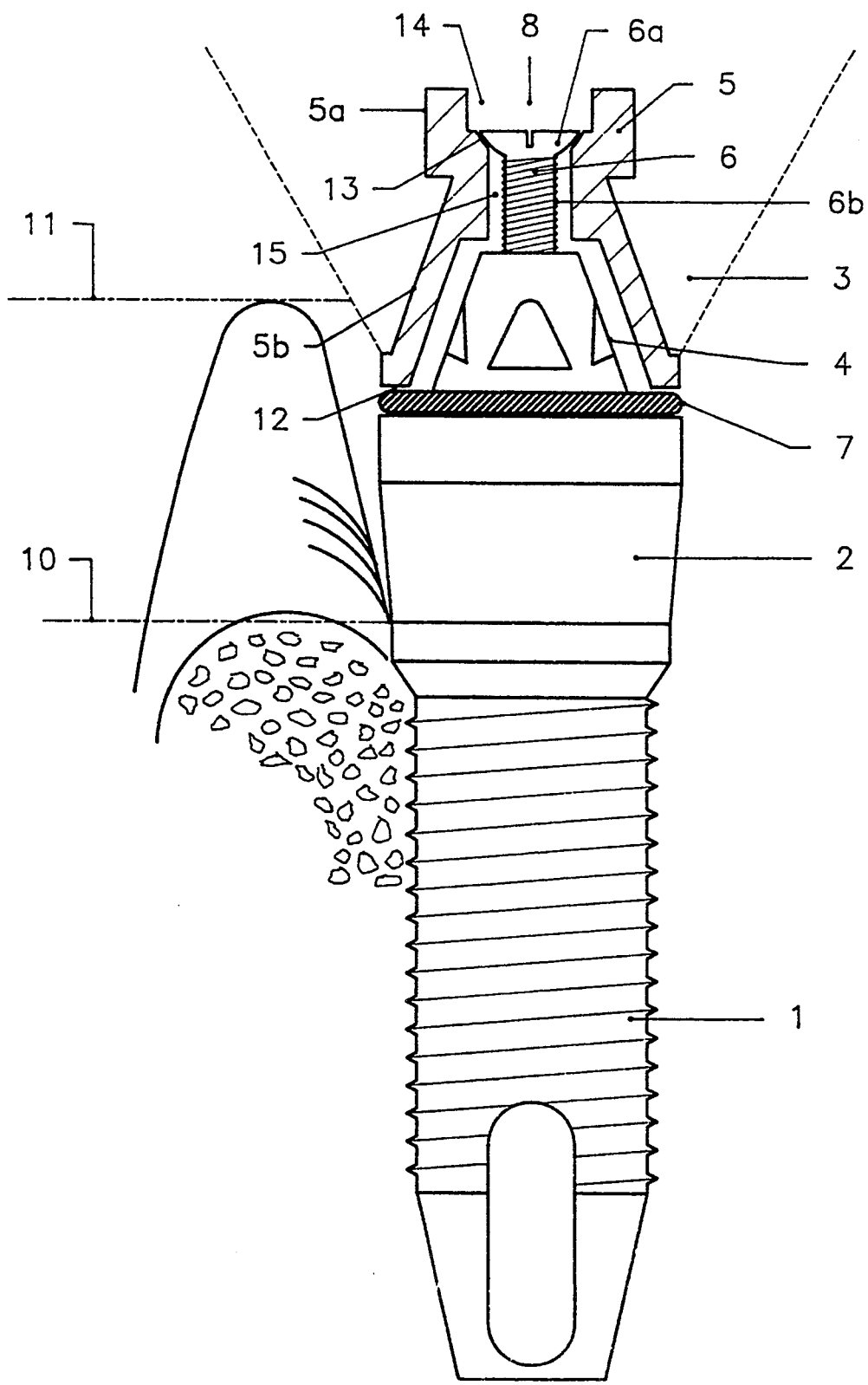
FIG. 1 is a front cross sectional view of the complete assembly showing the fixture, abutment and prosthesis.
Figure 2:
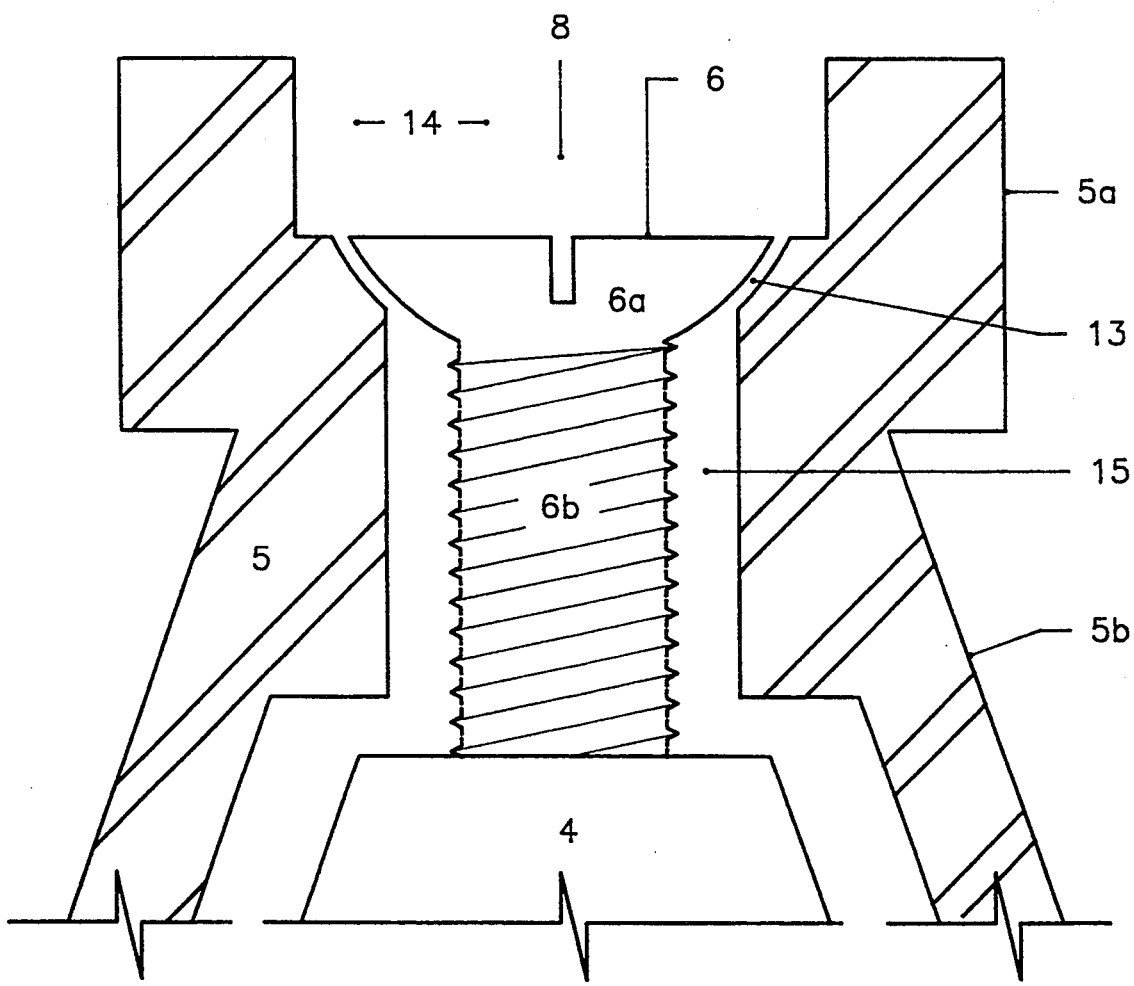
FIG. 2 is frontal view of the prosthesis.

In FIG. 1 there is seen an implant fixture 1 which is screwed into the jawbone J to the level indicated by line 10. The abutment 2 is screwed into fixture 1 by an abutment retaining screw having outwardly tapered head 4 and threaded shaft 4a. In the case of a 2 mm abutment the height of the crest of the gingiva would typically be at line 11. Note that the components described thus far constitute the prior art. The abutment is the "tapered" type. The invention is designed to be adapted to other abutment types for example, the standard and the conical.

Figure 3:
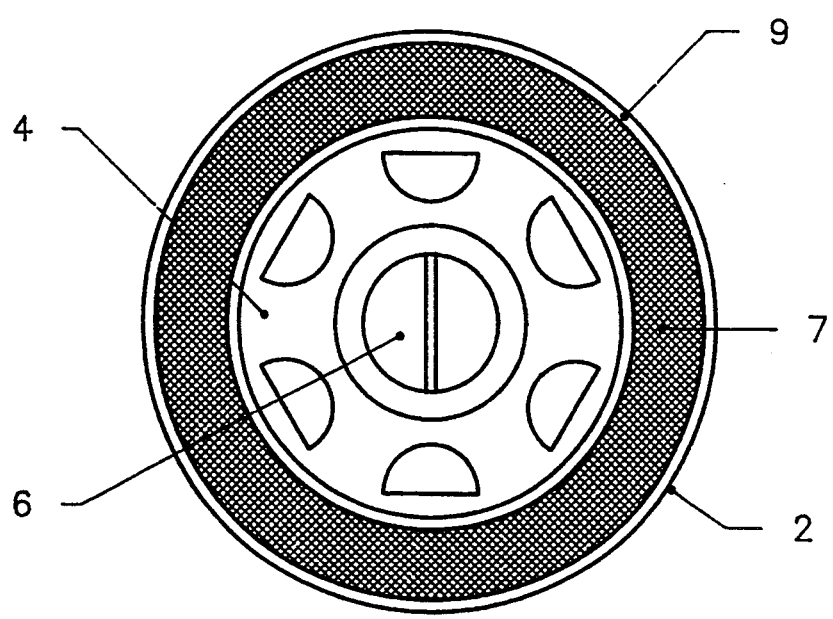
FIG. 3 is a plan view showing the retention screw, the tapered abutment screw and the tapered abutment.

Gasket 7 rests on the outer perimeter of the distal surface of the abutment. The gasket is made of an elastic material such as polyoxymethylene. The inner aspect of the gasket is round, precisely matched to fit around the abutment retaining screw head as seen in FIG. 3. The gasket is a flat washer-shaped circular construct with slightly rounded edges and is 0.75 mm in height. The gasket will have a modulus of elasticity such that the 0.75 mm height compresses approximately 0.1 mm in response to normal occlusal forces. This degree of stiffness would not allow any significant compression during normal hand tightening of the prosthesis retention screw. The gasket will have minimal water solubility and minimal water absorption so as to avoid dimensional change. It will have minimal porosity, to eliminate bacterial growth. It will have a lifetime retaining its full elastic properties measured in 10 to $10^{10}$ cycles. This gives a clinical lifetime of one to three years before any loss of elastic properties occurs. The gasket material will be white or grey in color if compatible with the other properties.

The prosthesis includes an assembly having a portion 5 made of precision machined gold alloy construct and a portion 3 made of porcelain and cast to portion 5. The head 5a of the prosthesis is cylindrical and the remainder 5b devolves into a truncated cone. The truncated cone has a proximal surface 12 which is flat and rests on the distal surface of the gasket. This bearing surface is responsible for transmitting occlusal forces to the gasket. The prosthesis has a non-threaded channel 15 running through its center for the prosthesis retaining screw 6. At the distal surface of this channel is a cradle 13 which is countersunk and fits precisely to the proximal rounded surface of the screw head 6a when screw shaft 6b has engaged the abutment head. The channel 15 is also free from any contact with the prosthesis retaining screw. The rounded screw head 6a takes the form of an arc of a circle, the center 8 of the circle lying 2 mm from the point where the screw head meets shaft 6b, thus forming the screw head on the arc of a 4 mm circle. A screw access channel 14 directly above the cradle provides an opening to allow placement and retrieval of the retention screw, which in turn allows placement and removal of prosthesis 3. The internal contours of the prosthesis provide a 0.5 mm relief from the centrally located tapered abutment screw and the shaft of the retention screw.

Under function resulting from occlusal forces, the fixture, the abutment, the abutment screw, and the prosthesis retention screw all remain rigid as in any current implant system. The prosthesis 5 is, however free to move axially, rotationally or any combination thereof. The cradle of the prosthesis 5 either moves bodily away from the prosthesis retention screw head or it rotates along the curve of such head, in both cases compressing the gasket. This action serves to mimic the function of the periodotal ligament in natural teeth.

It will be understood by those skilled in the art that various modifications may be made in the components described in this invention without departing from the scope of this invention as claimed.

We claim:

1. An intramobile element for dental implants comprising:
   a. a prosthesis, an abutment and a fixture,
   b. said prosthesis having an assembly and a member and a member cast to said assembly, said assembly having inner walls and including an upper cylindrical head which devolves to a truncated cone, a screw access channel extending from the top of said head to a rounded cradle countersunk at the proximal surface of said channel, a retaining screw having a rounded head fitting precisely in said cradle and a threaded shaft extending downwardly through a non-threaded channel into an abutment screw head of an abutment screw, said abutment screw having a threaded shaft that connects said abutment to said fixture, said truncated cone having a flat bottom surface, c. a flat, circular, elastic gasket having rounded outer edges and an inner circular opening that fits precisely around said abutment screw head and through which said threaded shaft of said abutment screw passes, said gasket being 0.75 mm in height and having a modulus of elasticity such that said gasket will compress 0.1 mm in response to a normal occlusal load, said gasket being neatly positioned at the perimeter of said abutment and between said assembly and said abutment, said retaining screw, and said abutment screw head being spaced from said inner walls of said prosthesis assembly allowing for rotation of said prosthesis under lateral occlusal forces.

2. The intramobile element of claim 1 wherein said elastic gasket is made of poly-oxymethylene, said cylindrical head, truncated cone, and retaining screw are made of gold alloy and said cast member is made of porcelain.

3. The intramobile element of claim 1 wherein said abutment is downwardly and inwardly tapered.

4. The intramobile element of claim 1 wherein said gasket is located in a hygienically desirable supragingival position.

5. The intramobile element of claim 1 wherein said gasket is located in an aesthetically desirable subgingival region having a distal surface and a proximal surface.

6. The intramobile element of claim 5 wherein the gasket is located 2 mm below the said distal subgingival surface so as to be invisible.

* * * * *